(12) United States Patent
Brankovic

(10) Patent No.: US 10,159,435 B1
(45) Date of Patent: Dec. 25, 2018

(54) EMOTION SENSOR SYSTEM

(71) Applicant: Novelic d.o.o., Belgrade OT (RS)

(72) Inventor: Veselin Brankovic, Belgrade (RS)

(73) Assignee: Novelic d.o.o., Belgrade (RS)

( * ) Notice: Subject to any disclaimer, the term of this patent is extended or adjusted under 35 U.S.C. 154(b) by 0 days.

(21) Appl. No.: 15/719,562

(22) Filed: Sep. 29, 2017

(51) Int. Cl.
| | |
|---|---|
| A61B 5/16 | (2006.01) |
| A61B 5/0205 | (2006.01) |
| A61B 5/00 | (2006.01) |
| A61B 5/05 | (2006.01) |
| A61B 5/024 | (2006.01) |
| A61B 5/08 | (2006.01) |

(52) U.S. Cl.
CPC .......... A61B 5/165 (2013.01); A61B 5/0205 (2013.01); A61B 5/7225 (2013.01); A61B 5/7278 (2013.01); A61B 5/024 (2013.01); A61B 5/0507 (2013.01); A61B 5/0816 (2013.01); A61B 2503/40 (2013.01); A61B 2560/0204 (2013.01)

(58) Field of Classification Search
CPC ..... A61B 5/165; A61B 5/0205; A61B 5/7225; A61B 5/7278
USPC ...................................................... 340/573.1
See application file for complete search history.

(56) References Cited

U.S. PATENT DOCUMENTS

| | | | |
|---|---|---|---|
| 6,190,314 B1 * | 2/2001 | Ark | G06F 9/451 600/300 |
| 8,764,656 B2 * | 7/2014 | Shin | A61B 5/0059 600/301 |
| 9,329,758 B2 * | 5/2016 | Guzak | G06F 3/0484 |
| 2011/0040155 A1 * | 2/2011 | Guzak | A61B 5/16 600/300 |

(Continued)

FOREIGN PATENT DOCUMENTS

| | | |
|---|---|---|
| CN | 203290919 U | 11/2013 |
| CN | 103583398 U | 2/2014 |

(Continued)

*Primary Examiner* — Omar Casillashernandez
(74) *Attorney, Agent, or Firm* — Luoh J. Wu; Continent Patent Office LLP

(57) ABSTRACT

The present invention discloses a mm-wave radar sensor to be deployed as emotion sensor, being inherently small size, and being able to be produced in low cost manner. The key system relevant components are utilization of mm-wave integrated radar, specific planar high-gain antenna radiation patterns, and analyzing the vital signs of objects by the same apparatus. The objects are human beings with vital signs vibrations, and animals with vital sign vibrations, where the system calculates and detects the frequency of vital sign rates: heartbeats and respiration frequencies. The values of vital signs rates as well as the changes of vital sign rates are used together with objects vital signs profile to calculate the emotion value. Emotion value may be additionally enhanced by specific movement pattern events added additionally in the emotion status evaluation. Emotion value can be information about object mood or simple alert of the excitements (Continued)

or calmness, as well as information of the increased or decreased excitement. Preferably, the proposed apparatus is using 60 GHz ISM Band integrated radar front, working in Doppler mode. Physical size of proposed apparatus in range: 4×2×1 cm or smaller.

9 Claims, 6 Drawing Sheets

(56) References Cited

U.S. PATENT DOCUMENTS

| | | | |
|---|---|---|---|
| 2012/0116186 A1* | 5/2012 | Shrivastav | A61B 5/0507 600/301 |
| 2012/0130196 A1* | 5/2012 | Jain | A61B 5/0022 600/300 |
| 2014/0112556 A1* | 4/2014 | Kalinli-Akbacak | G10L 25/63 382/128 |
| 2014/0171752 A1* | 6/2014 | Park | A61B 5/165 600/301 |
| 2016/0374605 A1* | 12/2016 | Pandian | A61B 5/0205 600/323 |
| 2017/0311861 A1* | 11/2017 | Pan | A61B 5/02444 |
| 2017/0311901 A1* | 11/2017 | Zhao | G06F 19/3418 |
| 2018/0000359 A1* | 1/2018 | Watanabe | A61B 5/0261 |

FOREIGN PATENT DOCUMENTS

| | | |
|---|---|---|
| EP | 2060228 A | 5/2009 |
| WO | 005043453 A2 | 5/2005 |
| WO | 2014071062 A2 | 5/2014 |

* cited by examiner

EMOTION SENSOR SYSTEM

TECHNICAL FIELD

The present invention relates to an emotion apparatus and method of operation comprising a mm-wave radar with planar high-gain antenna systems, utilizing information extracted from vital signs detection, where vital signs are heartbeat rate and respiration rate, and processing this information to get the information about emotions of the object under observation. Typical emotion information extraction results are: increased probability of detecting calmness and excitement as two clearly distinguishable feelings, as well as the mood swing between calmness and excitement, or increased or decreased excitement. The emotion extraction is done without physical contact to the object, where the object is a human being or an animal.

BACKGROUND ART

There is a strong motivation to deploy the contactless, very small-size, low-power and very low-cost sensors for the emotion detection in following application scenarios:
   a) Detection of a human, being excited, without physical contact to the person;
   b) Detection of a human, being calm, without physical contact to the person;
   c) Detection of a mood or emotional status of a human, being defined as condition between being excited and being calm on the specific linear scale, without physical contact to the person;
   d) Detection of an animal being excited without physical contact to the animal;
   e) Detection of the animal being calm without physical contact to the animal;
   f) Detection of a mood or emotional status of an animal, being defined as condition between being excited and being calm on the specific linear scale, without physical contact to the person;
   g) Detection of a human mood changes, being defined as an emotional status change between being excited and being calm on the specific linear scale, without physical contact to the person;
   h) Detection of the animal mood changes, being defined as an emotional status change between being excited and being calm on the specific linear scale, without physical contact to the animal;

The related apparatus and method of operation should be able to initiate the related actions, depending on a detected emotional status or pre-defined event.

State-of-the-art emotion sensors are based on contactless and contact-based sensor acquisitions. The contactless emotion sensors are usually based on the optical video assessments of the object under observation, or on the combination of the different art of information, obtained by different art of sensors.

It was published in different scientific articles that microwave radar sensor, in the frequency range 3-30 GHz, may be used to detect the vital signs. Especially 2.4-, 3-10, 24- and 60-GHz vital sign demonstrators have been publicly reported.

The following patents and patent applications published in the last couple of years show the relevance of the topic and the state-of-the-art of the emotion sensors solutions.

U.S. Pat. No. 8,764,656, "Sensing device of emotion signal and method thereof" describes the sensing device of an emotion signal and a method thereof capable of recognizing and analyzing the change in emotion by collecting at least one of the bio signals and peripheral environmental signals. The approach considers PPG sensor, a GSR sensor, a temperature/humidity sensor, an acceleration sensor, a voice sensor, and an infrared sensor as means to get the emotional information.

US 20140112556, "Multi-modal sensor based emotion recognition and emotional interface" from Sony Corporation describes the system using one or more acoustic features, visual features, linguistic features, and physical features extracted from signals obtained by one or more sensors.

CN 203290919, "Novel pressure sensor set for implicit emotion interaction cushion", describes comprises forty pairs of pressure sensors system assessing the movements of the body under observation.

WO 2014071062 "Wearable emotion detection and feedback system", describes head mounted display and sensing apparatus cooperating with the display detect audible and visual behaviour of a subject. During interactions, the device, recognizes emotional states in subjects by comparing detected sensor input against a database of human/ primate gestures/expressions, posture, and speech.

U.S. Pat. No. 6,190,314, "Computer input device with biosensors for sensing user emotions" by IBM, describes a method and system for correlating physiological attributes including heart rate, temperature, general somatic activity (GSA), and galvanic skin response (GSR) to N emotions of a user of a computer input device, such as a computer mouse.

US 20140171752, "Apparatus and method for controlling emotion of driver" describes an apparatus for controlling emotion of a driver includes an emotion sensor unit configured to collect a biomedical signal from the driver. The emotion sensor unit comprises an image recognition apparatus to recognize a face, a gesture and a state of a pupil of the driver, a voice recognition apparatus to recognize a voice of the driver, and a contact sensor.

WO 2005043453, "Robust and low cost optical system for sensing stress, emotion and deception in human subjects" by Northrop Grumman described a method and related apparatus for sensing selected emotions or physical conditions in a human subject. The technique employs a two dimensional camera to generate a facial image of a human subject.

CN 103583398, "Dog emotion-relieving collar" discloses a dog emotion-relieving collar comprising a control chip, a pulse meter, a sound sensor, a flash memory and a loudspeaker as a means of the animal emotion information extraction.

EP 2060228, "Medical device with an emotion measuring finger sheathing means incorporating with a long-distance control" describes contact based system with object using information about temperature.

This invention introduces apparatus and method operation for emotion sensor, based on mm-wave radar sensor, digital signal processing, high-gain planar antenna systems, which is inherently small size, inherently low cost and which allowed contactless detection of the emotional status of a human being or animal, from the distance up to several meters; typically 0.5 to 1 meter.

SUMMARY OF INVENTION

This invention proposed apparatus 100 and method of operation for emotional sensor, being able:
   To detect the emotional status of the object at the distance from tens of millimeters to several meters, by issuing actions and information exchange, where the objects are human beings or animals;

To be inherently very small in size, compared to state of the art;

To be inherently very low cost, compared to state of the art;

To have wired or wireless interface to the entity to transmit information about event, or emotional status;

To have ability to initiate the specific actions upon detection of the specified pre-event events, being related to the emotional status;

To be integrated in the more complex systems, with the plurality of applications.

The key system-relevant components of the proposed apparatus 100 are:

High-gain planar antenna system, realized by the plurality of the technologies, with each of the transmit 21 and receiving 22 parts having more than one antenna radiation element and the radiation diagram in the direction of the seat.

Millimeter-wave radar with integrated front end on silicon 10, system on chip, providing analog processing of the mm-wave signal, and the provision of the analog to digital conversion functionality;

Digital signal processing functionality 40, having standardized physical digital interface 60, with plurality of the realization;

Mechanical assembly with power supply interface to power supply infrastructure, containing mechanically integrated antenna, digital and analog functionalities and having mechanical connection;

Supporting circuitry 50 as a part of apparatus 100 may include functionalities like loudspeaker and light warning source, by the plurality of the realization options;

Optional wireless communication systems may be attached, to provide information of the emotion status remotely.

The proposed apparatus and method of operation allow and facilitate production of the complete sensor systems in the cost range lower than 10 € per piece for higher quantities, which presents at least one order of magnitude cost difference compared to current state-of-the-art solutions. This is possible only by using proposed integrated circuitry and antenna systems.

The choice to use the mm-wave frequency band (30 GHz to 300 GHz) and advantageously to use 60 GHz band is mainly related to the size of the antenna system allowing very small and compact device, even though it contains the high-gain antenna with more than one radiation elements. Millimeter-wave front end preferably operates in 60 GHz ISM Band, under short-range device regulation, allowing the world-wide usage without dedicated frequency band allocation. The usage of the 77-79 GHz mm-wave frequency bands or higher mm-wave ISM bands is also possible. However, the detection distance in that case will be probably smaller, due to higher radio waves attenuation at higher frequencies.

The proposed system has technical capability and specific Method of operation to detect the heartbeat and respiration frequency of the object and to process this information, to extract the emotion status of the object, where the status includes the probability related information of the a) Excitement or calmness, or linear rate between this two opposite statuses;

b) Change of the mood, changing of the emotions by detecting speed of changing the emotional behavior of the object.

The event to be detected may be:
1. There is an excitement of a person or an animal;
2. The person or animal under observation is calm;
3. The person & animal under observation is getting more excited;
4. The person & animal under observation is getting less excited;
5. The person & animal under observation experiences mood swing, where there is a mood scale covering full excitement at one end(high), and full calmness at the other end(low).

The Apparatus 100 may be:
1. Used as fixed in the transportation vehicle environment observing the person;
2. Used as fixed in the living or medical recovery or entertainment or leisure environment of the person under observation, as separate independent device;
3. Integrated in fixed multimedia equipment facing person under observation, like TV sets, computer displays, or smart displays;
4. Integrated in mobile multimedia equipment facing person under observation, like portable PCs, smart mobile phones and tablets;
5. Used as wearable device, where one person may observe the second person;
6. Used as portable device, where one person may observe the second person or animal;
7. Used as fixed device, where human beings are observed, where the human beings may pass through the control point;
8. Used as fixed device, where animals are observed, where the animals may pass through the control point;
9. Used as fixed or portable device, for security or safety reasons, by observing the person standing in front of dedicated control point, or in front of the person performing conversation with the observing person.

The Apparatus 100 main purpose could be to:
1. Detect emotional status of the person, and impose the activation of the measures, which will bring the emotional status of the person into different mood. For example: The person is under influence of multimedia content, or under influence of light level, or audio level and by changing multimedia content, or light & audio level & music rhythm & music art, we will influence the person, and may achieve changing of his mood. Changing of the mood may target to make the person calmer when excited, to make the person "awake" when being too calm or to make the person being more excited.
2. Detect the emotional profile of the person & animal under observation, in order to detected abbreviations, in qualitative and quantitative manner, of the typical emotional behaviour in dedicated time frame or moment.
3. Detect the emotional status of the person & animal, comparing them with general non dedicated person related profiles, by simple measurement assessments. This is related especially for security & safety applications. In this case, the person being excited among the persons, without special excitement may be detected. Typical examples, could be detected smuggling person in from of custom area, making excitement alerts people on pass control checking immigration, check of the security people with badges having emotion sensors on their cloths to the suspicions people, they are speaking, contactless excitement control of the people, in investigative actions, and others.

4. Detect the emotional status of the observing person, in front of person having wearable sensors, for entertainment and leisure purpose. For example to see if the observing person is emotionally reacting by approaching you with presence of the person having Apparatus 100.

Means of using specific radiation Tx, RX antenna shapes is proposed, as well as means of optional wireless connectivity of the Apparatus 100.

BRIEF DESCRIPTION OF DRAWINGS

FIG. 1a shows person under emotion observation in the transportation vehicle of the general art.

FIG. 1b shows person under emotion observation, with Apparatus 100 attached to second person, performing emotional observation.

FIG. 1c shows person under emotion observation, with Apparatus 100 with fixed position as part of the fixed multimedia equipment or display, or as a part of the infrastructure for assistive living.

FIG. 1d shows person under emotion observation, with Apparatus 100 being integrated in the portable multimedia device: tablet, smart phone, PC, communication device general art.

FIG. 1e shows persons under emotional observation, with Apparatus 100 evaluating emotional status of the people passing by or staying in specific positions, like front desks at immigration office or similar.

FIG. 1f shows animals under emotion observation, with Apparatus 100 evaluating emotional status of the animal in their living environment or by passing specific control pints.

FIG. 1g shows pets under emotion observation, with Apparatus 100 evaluating emotional status of the pet in their living environment.

DESCRIPTION OF EMBODIMENTS

Figure 1:
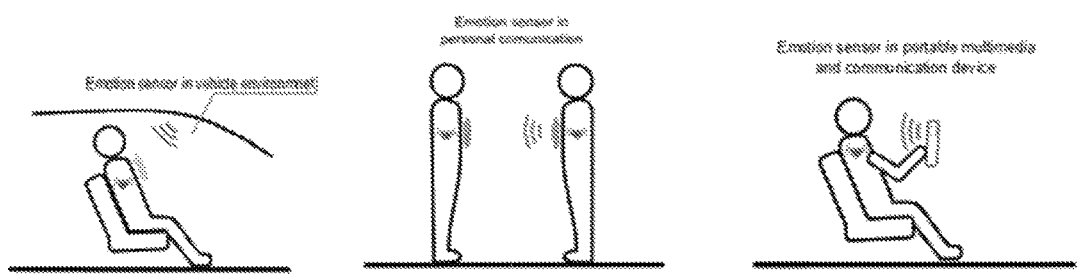
FIG. 1 presents apparatus typical application scenarios, where.
Figure 1:
Figure 1:
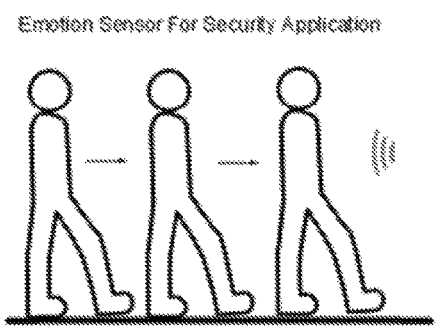
Figure 2:
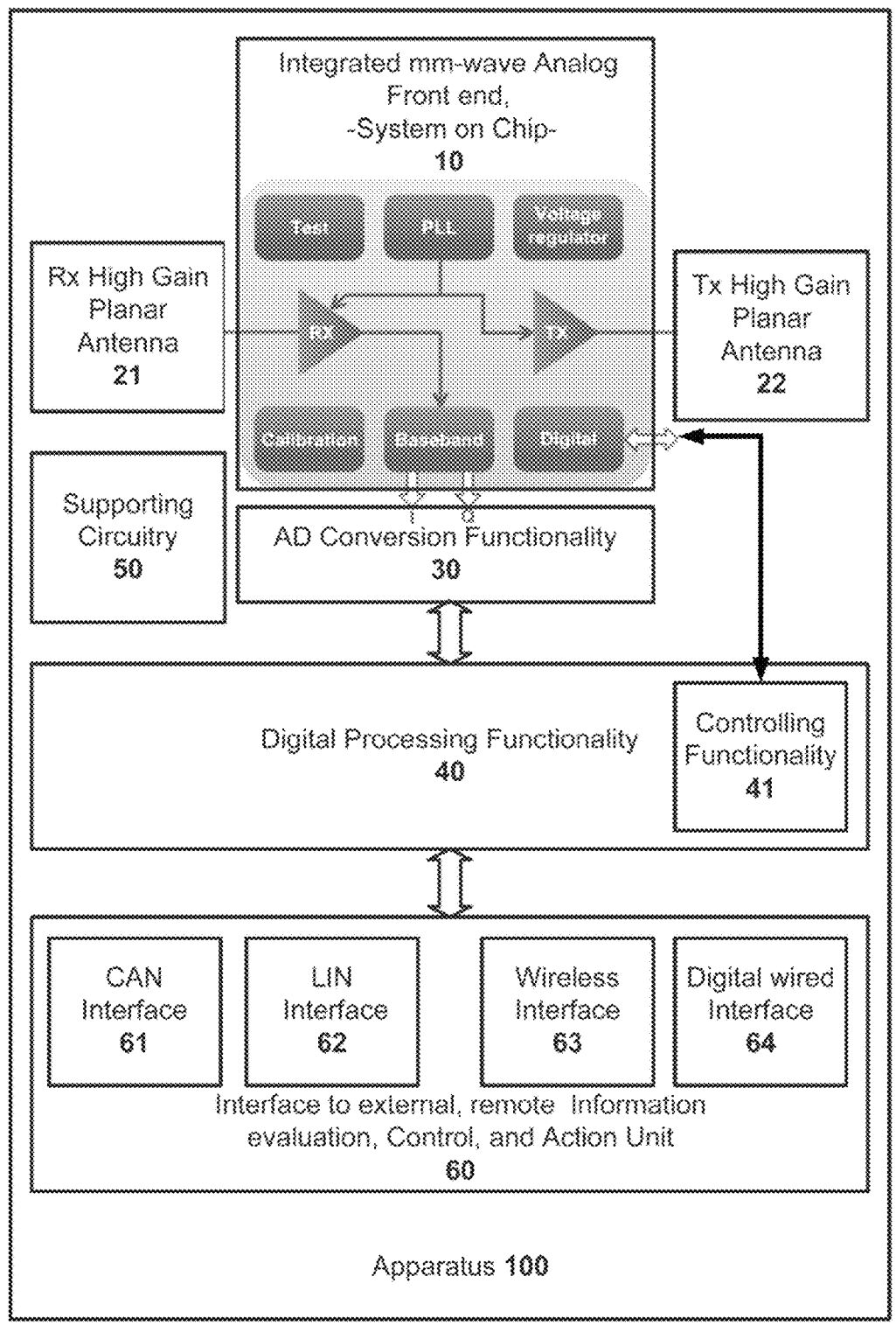
FIG. 2 presents apparatus functional block diagram.
Figure 3:
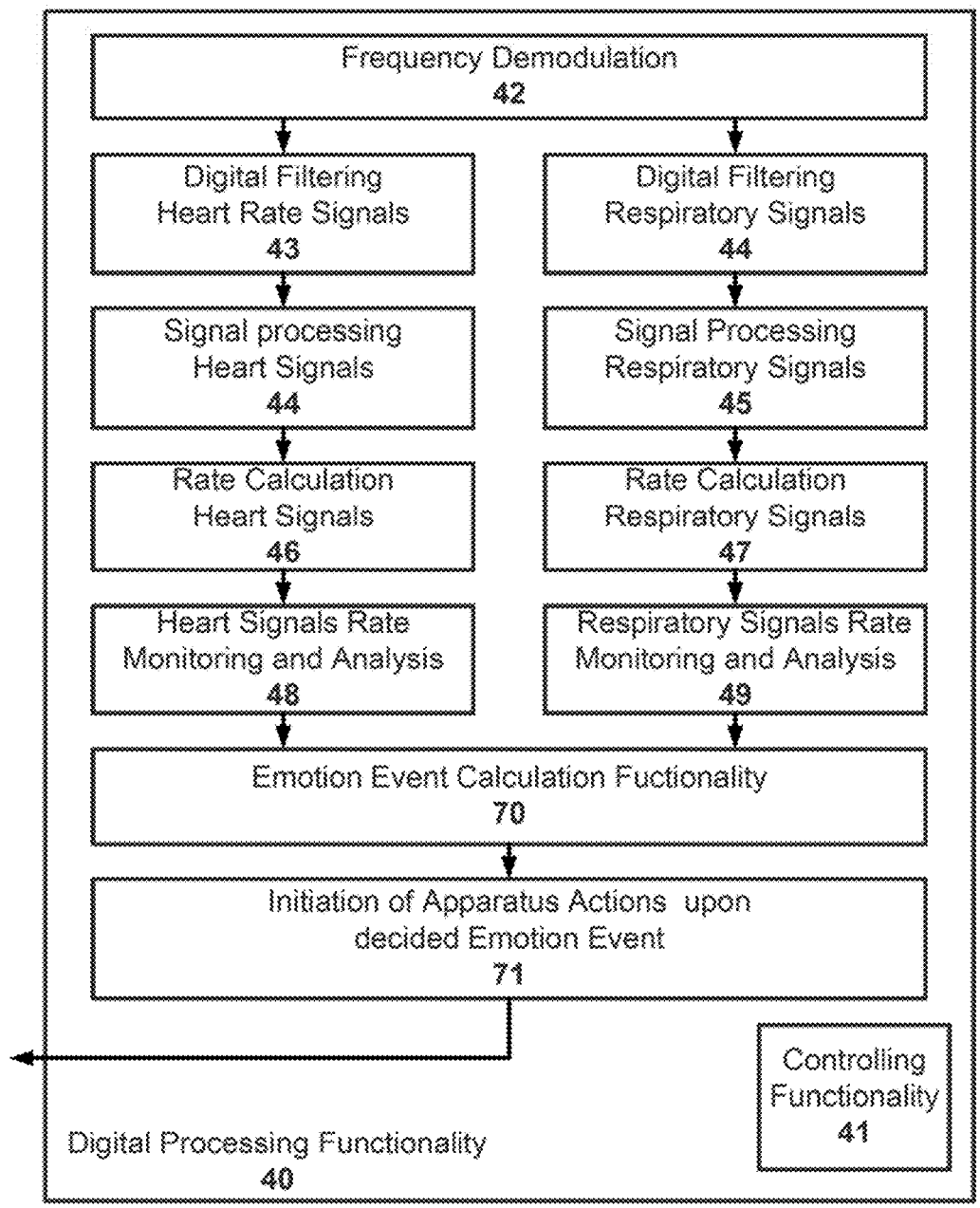
FIG. 3 presents apparatus digital processing functional blocks.
Figure 4:
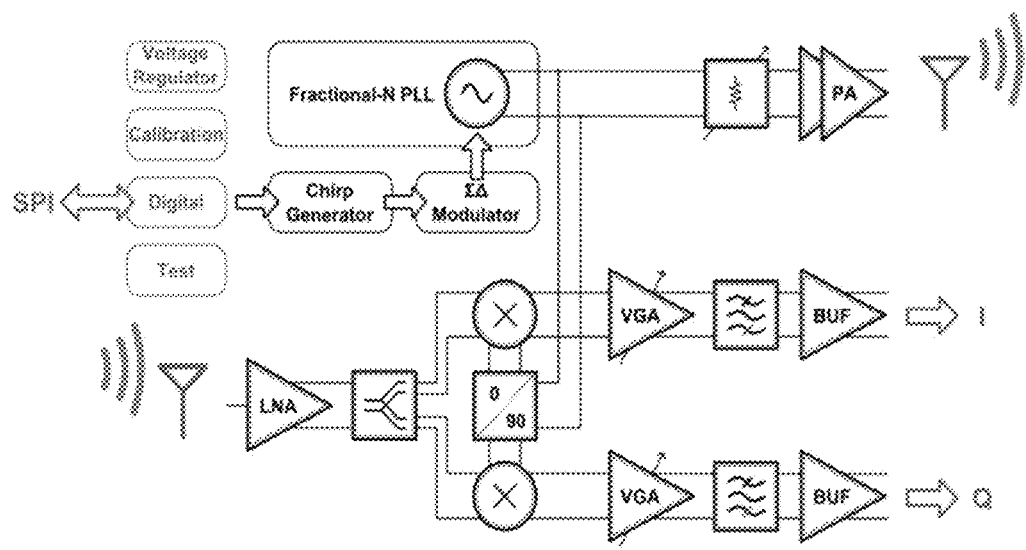
FIG. 4 presents integrated mm-wave front end block diagram.

Apparatus 100 is preferably observing dedicated area in its front, having Line-of-Sight (LOS), i.e. as shown in the FIG. 1a, FIG. 1b, FIG. 1c, FIG. 1d, FIG. 1e, FIG. 1f and FIG. 1g. FIG. 1a discloses the use scenario of the Apparatus 100, being integrated in the general transportation environment. This may be particularly applied for environment like personal vehicles, trains, busses, airplanes and ships. The typical application could be to react by proving dedicated multimedia content to the passenger, or to include light and sound conditions, or to alert the transportation assistance if some specific emotional discrepancy appears. FIG. 1b discloses the use scenario of the Apparatus 100, being used in personal communication, where the observing person may be aware of the emotional reaction of the observed person on the speech content or on a simple present of the observing person, coming close to the observed person, and observed person is getting aware of the physical presence of the observing person. FIG. 1c discloses the use scenario of the Apparatus 100, being used in daily life of the observed person as for example at his home. In this case the emotion sensor could be integrated in the TV set and the multimedia content being provided to be observed person may be adapted, to its emotional behaviour or his mood. On the other hand, this approach may be used also in assistive living manner, where the room light conditions and audio level are adopted to the emotional status of the observed person. In all cases optional wireless communication means, by the plurality of its realizations, of the interface 60, would allow to transmit the emotional status of the observed person, further to the remote position, where specific further actions may be decided and remotely also optionally imposed. FIG. 1d discloses the use scenario of the Apparatus 100, integrated in the portable mobile device, which may be smart phone, tablet, portable PC, communication device or other device with or without display. In this scenario the portable device can react on emotion status of the observed person and provide specific multimedia content, or provide dedicated purchasing recommendation, or provide marketing actions in evaluation of specific content, being provided by portable device, or to transfer the emotional status of the observed person by own wireless means, to remote point, allowing actions being imposed by remote decision. FIG. 1e discloses the use scenario of the Apparatus 100 in typical security or safety relevant applications. The typical scenario discloses the contactless observation of the passengers or people at the airports, railway stations, and public areas, where they may pass through hidden or not hidden emotion sensor observation points. This may allow the security personal to be alerted on abbreviations in the excitement over the average public level, which may impose their reactions or further check of the persons. On the same time by immigration office control box, or by other entrance control points in the areas under specific control importance, the person with abbreviations from the average emotion level may be detected and further evaluated. FIG. 1f discloses the use scenario of the Apparatus 100, where the emotion status of animal is observed. This may be applied for pets, with Apparatus 100 is being installed close the areas where the pets usually are, where the Apparatus 100, has emotion profile of the animal, being calculated over specific longer observation of the pet. On the other side emotion of the expensive animals like horses or cows has a practical relevance in keeping them in good mood and health. FIG. 1g shows emotion observation of the pet in the home environment. The piece of information on the predefined emotional discrepancies compared to the pet profile, may be communicated by the plurality of wireless and wired means to the animal control unit or pet owner.

In all cases the excitement and calmness are related to the combination of the detected values related to the heartbeat rate and respiration frequency of the person or animal under observation, where both of these vital signs indicators or one of them is practically used in the process of the emotion calculation.

Due to proposed mm-wave radar application, the size of the high-gain antenna System for RX 21 and for TX 22 is small enough to allow practical use of the apparatus while maintaining high-gain antenna features. Taking into account proposed 60 GHz ISM band operation, or alternatively higher mm-wave operation bands. The approximate size of the Apparatus 100 is related mainly to the size of the Tx 21 and Rx 22 implementations options. The size of the Apparatus 100 may be in range of 4×2×1 cm or smaller.

The crucial block of the proposed apparatus 100 is the Integrated mm-wave front end,—System on Chip-10. It contains the complete RF functionality, and includes power amplifier functionality attached to the antenna system 22, low noise amplifier attached to antenna system 21, integrated PLL, used both for up-conversion in transmit and down-conversion in receive, providing two analog pre-filtered signals as IQ outputs to A/D conversion functionality 30. The entity 10 has test functionality, voltage regulation, and digital interface to the Controlling functionality 41, which is a part of the Digital Processing functionality 40. More detailed structure of the integrated front end 10 is given in Fig. The use of the integrated front end 10 allows the system to be compact and have low-cost assembly, enabling the use in the real product. Integration of the complete frequency synthesis and complete analog functionality in a single chip allows considerable reduction of the cost, which is not the case in published mm-wave systems. The entity 10 is preferably realized using SiGe BiCMOS technology that provides high performance. Alternatively CMOS technology may be used. AD (analog to digital) conversion functionality 30 converts the two quadrature signals, I and Q, which are the outputs of the entity 10, and feeds digital representation of those signals to the Digital processing functionality 40 for further processing. Entity 30 is realized by plurality of the realization options, with sampling frequency typically under 1 MHz and typically at least 8 bit resolution for the vital signs detection applications. Entity 30 may be integrated on the same chip as Entity 10. Entity 30 may be integrated on the same chip as Entity 40. Entities 40, 10, and 30 may be all integrated on a single chip. Entity 60 is providing digital interfaces to outside world. They may be typical vehicle & industrial wired interface like CAN interface 61, and/or UN interface 62, or custom digital interface 64. Optional digital wireless interface 63 is outlined. Supporting circuitry 50 optionally includes additional memory, manual switching, power supply regulation circuitry, mechanical support, and any additional functionality required for easy integration, during manufacturing. The mechanical support structure for integration of all functionality is preferably provided using advanced polymer technologies to minimize the assembly production cost. Optionally, entity 50 may also include battery, optional acoustic warning systems with loudspeakers or other means of warning light sources, allowing autonomous operation.

Digital processing functionality 40 may be realized by the plurality of technologies, such as: advanced CPUs, FPGAs, advanced µC, DSP, or ASIC, or their combinations, where the digital processing may be performed by "soft" approach or by hard-wired approach or by their combination. Preferably functionalities 60 and 40 are integrated on a simple ASIC, having CPU on one digital SOC. Digital processing functionality 40 includes functionalities 41, and 70-71 as described in Fig.

The first part of the Method of Operations is related to the vibration detection, where the Doppler principle is utilized. The FMCW radar analog parts are realized within integrated mm-wave front end 10, which is used in Doppler mode, where fractional PLL is assigned to produce only one operation frequency. The system concept is that PLL on the chip may be address to allow the Doppler operation in the arbitrary frequency with operation band of the system. That means, that many such Doppler sensors may advantageously simultaneously used, being close to one to another. Example, in the bus or other transportation means, where each seat may have the different operation frequency, and the sensor systems will not interfere with other sensors. In the proposed invention the vital signs as vibrations, are detected, being related to human being or animal under observation. The breathing and heartbeats are imposing small body movements, which we would like to address by remote contactless sensing. The entity 10 sends mm-wave CW signal by Tx antenna entity 22 towards the body. The radio signal of mm-wave frequency does not penetrate the clothes and the human body. Heartbeat and respirations cause body micro-movements. According to Doppler effect those signal are causing frequency modulation of the radio signal received by the antenna entity 21. After the IQ demodulation, i.e. mixing with the quadrature of the transmitted signal, and subsequent low-pass filtering, performed in the entity 10, the low-frequency baseband signals are provided to the entity 30. These two analog signals are converted into corresponding two digital streams by the entity 30 and fed into the entity 40. In entity 42 additional low-pass digital filtering may be performed. In 43, appropriate digital band-pass filtering such that the expected heartbeats are in-band is performed. Filter characteristics must account for the expected variations of the appropriate biomarkers which reflect class of the human beings, like adults, kids, and animals. Filtering characteristics may be set based on the biomarkers history and statistics, previously stored in memory. Filtered signals are first converted in the frequency domain. The corresponding heartbeat rates or respiration frequencies are detected as peaks in signal spectrum by using entity 46. The position of the peaks determines the corresponding rate. The plurality of peak detection methods may be utilized, with corresponding digital signal processing realizations of various averaging, smoothing, windowing and peak position estimation techniques. The entity 48 is picking detected vital signs information. This information is provided to Entity 70, which is responsible for emotion event decision.

Figure 5:
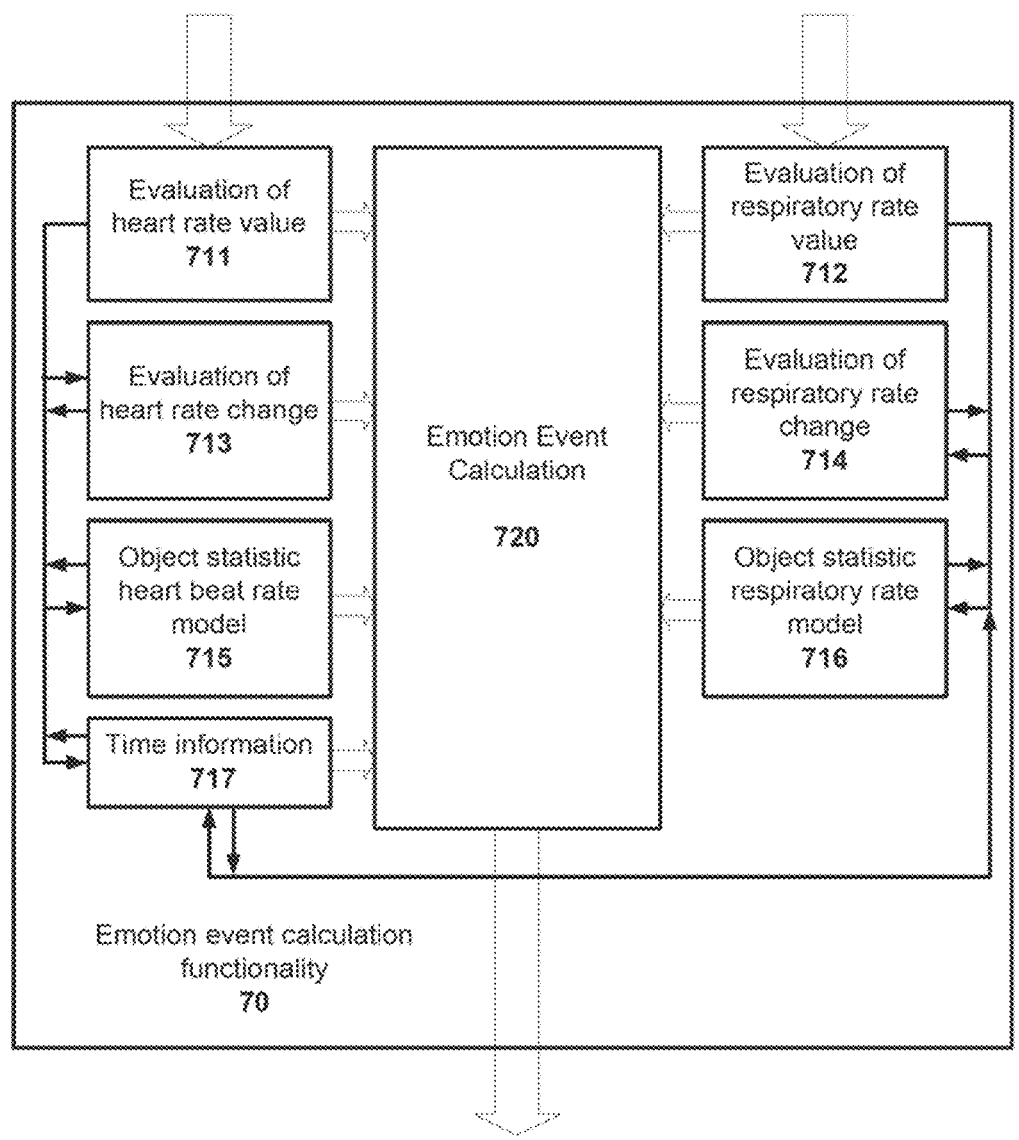
FIG. 5 presents logical functional blocks of the emotion event detection functionality 70, being related to the FIG. 2.

Entities 48 and 49 are detecting changes, which may be declared after analysis as movements. This information is fed to the entity 70. The entity 70 functional blocks are shown in the FIG. 5. Entity 711 evaluates the values of the detected heartbeats, and entity 712 evaluates respiration frequencies. Entities 713 and 714 are calculating heartbeat rate change, and respiration frequency change, respectively, and they are performing evaluation of the rate changes. The change is calculated by plurality of the mathematical numerical methodologies for first derivate calculation. Information about change rates is provided with entities 715, and 716 respectively, together with vital signs rates information from entities 711 and 712. 715 and 716 are building object behavior profile regarding vital signs rates, and vital sign rates changes, with related time stamps, coming from entity 717. Depending on application scenarios of the proposed invention, entities 715 and 716 can have external predefined statistical models for object classes. For examples, they may have the ranges of the typical statistic values for vital signs behavior of human being of animal, being related to different parts of the day, and/or in winter, summer, and/or geographical location. That means entity 720 obtains information about vital signs rates, vital signs rate changes, object vital signs profile with typical values of the rates, their changes with time information, time information and optionally also object general statistics data about vital sign rates, vital sign rate changes and with time information.

The entities 715 and 716 particularly provide the history of the heartbeat rate model and respiration frequencies for the person or animal under observation. The information particularly includes one or more information outlined:

Previous acquisition information of heartbeat rates over at least one predefined period Averaged information of heartbeat rates over at least one predefined period Rate of change information for heartbeat frequency in specific predefined time windows Previous acquisition information of respiration frequency rates over at least one predefined period Averaged information of respiration rates over at least one predefined period Rate of change information for respiration frequency in specific predefined time windows Comparison with thresholds for rates for both heartbeats and respiration frequencies related to person or animal profile of object under observation Comparison with thresholds for rates changes for both heartbeats and respiration frequencies related to person or animal profile of object under observation Optional comparison with thresholds for frequency rates for both heartbeats and respiration frequencies related to general statistic data of person or animal profile Optional comparison with thresholds for frequency rates changes for both heartbeats and respiration frequencies related to general statistic data of person or animal profile Time information is relevant for setting thresholds, due to typical vital signs values in sleeping time or "being awake" time. For example the threshold or detecting some specific excitement level may be different if the person is observed seating, in midnight time or seating in the same seat on noon time. That also means that the emotion profile of the person or animal under observation may have statistical data for vital signs, with the day time related time stamps.

Emotion event calculation entity 720 calculates the emotion level score based on a weighted sum of the following information set, with possible zero weights in case corresponding optional blocks are not present, or providing information is not feasible:

Heartbeat rate in the moment of evaluation

Heartbeat rate change in the moment of evaluation regarding pre-defined time window Respiratory rate in the moment of evaluation Respiratory rate change in the moment of evaluation regarding pre-defined time window Time information Object profile values for heartbeat rate, with statistically calculated values, for dedicated time, or part of the day, showing rate ranges regarding calmness, and rate ranges regarding excitements Object profile values for respiration rate, with statistically calculated values, for dedicated time, or part of the day, showing rate ranges regarding calmness, and rate ranges regarding excitements Object profile values for heartbeat rate changes, with statistically calculated values, for dedicated time, or part of the day, showing rate change ranges regarding calmness, and rate change ranges regarding excitements Object profile values for respiration rate, with statistically calculated values, for dedicated time, or part of the day, showing rate change ranges regarding calmness, and rate changes ranges regarding excitements Optional general human being or general type of animal profile values for heartbeat rate, with statistically calculated values, for dedicated time, or part of the day, showing rate ranges regarding calmness, and rate ranges regarding excitements Optional general human being or general type of animal profile values for respiration rate, with statistically calculated values, for dedicated time, or part of the day, showing rate ranges regarding calmness, and rate ranges regarding excitements Optional general human being or general type of animal values for heartbeat rate changes, with statistically calculated values, for dedicated time, or part of the day, showing rate change ranges regarding calmness, and rate change ranges regarding excitements Optional general human being or general type of animal profile values for respiration rate, with statistically calculated values, for dedicated time, or part of the day, showing rate change ranges regarding calmness, and rate changes ranges regarding excitements Optional general human being or general type of animal movement pattern, matching predefined movement pattern thresholds, for dedicated time, or part of the day.

The weighting factors are predefined or determined based on the information set, predefined values and behavior statistics. Weighting factor could be zero also if some piece of information is not provided due to signal processing mistakes, or if this value is not calculated in order to minimize the power consumption and the signal processing efforts of the sensor, to have cheaper signal processing hardware and therefore cheaper apparatus 100, with potential smaller capacity battery, if we have portable type of application. That means that the emotion status may be calculated only by information being related to heart signals or respiration frequency, only. For example, the heart rate is calculated to be over 200 bit/s, which is not feasible, but respiration rate is 20 per minute, which is feasible value, meaning that respiration rate and its derivate will be considered. On the other hand this may also means that the lowest level of the information, being required to get the emotion sensor, may be only heartbeat or respiration rate in dedicated moment of observation, without permanent calculation of the rate changes, only by comparing, previous rate conditions. In that case the emotion sensor status calculation entity 720, gives information: Excitement is increased or excitement is decreased. Those operation modes are typically predefined by specific settings and choice of the apparatus 100 processing and power supply components.

Entity 720 has capability to map the rates, rates changes if available, thresholds if available, time, and to issue one or more following information:

a) Excitement of the object increased or decreased;
b) Object is excited;
c) Object is calm;
d) Object mood is on the specific point on linear scale between calm and excited, regarding his personal profile;
e) Object mood is on the specific point on linear scale between calm and excited, regarding general pre-defined profile;
f) Object is getting excited;
g) Object is getting less excited;
h) Object mood change is on the specific point on linear scale between calm and excited, regarding his personal profile;
i) Object mood change is on the specific point on linear scale between calm and excited, regarding general pre-defined profile;

This emotion status information is communicated to the entity 71. Based on this information, the entity 71 is initiating predefined actions using entity 60 and/or entity 50. Entity 50 may have optional audio and/or optional visual indication and/or vibration/alerting capabilities to person performing or monitoring emotion sensing, which is especially related to the application scenarios of FIG. 1b, FIG. 1e and FIG. 1f.

If the apparatus detects the abrupt stop of the heartbeat confirmed with the cease of respiration activity, alerts may be initiated.

The radiation beam shape is important for the several reasons: due to the inherently low cost apparatus system cost and size the proposed antenna system has high gain antenna for transmit and receive chain, being realized by more than one radiation elements, typically without mechanical and/or electrical steering. More antenna gain means narrow beam, meaning lower space coverage as drawback, and longer detection distance as advantage. On the other hand the due to preferred usage in the ISM band the maximum gain of the antenna in specific direction multiplied with the transmit output power is a limited (EIRP). Feeding network causes more power losses in the case if the antenna system has more radiation elements.

Figure 6:
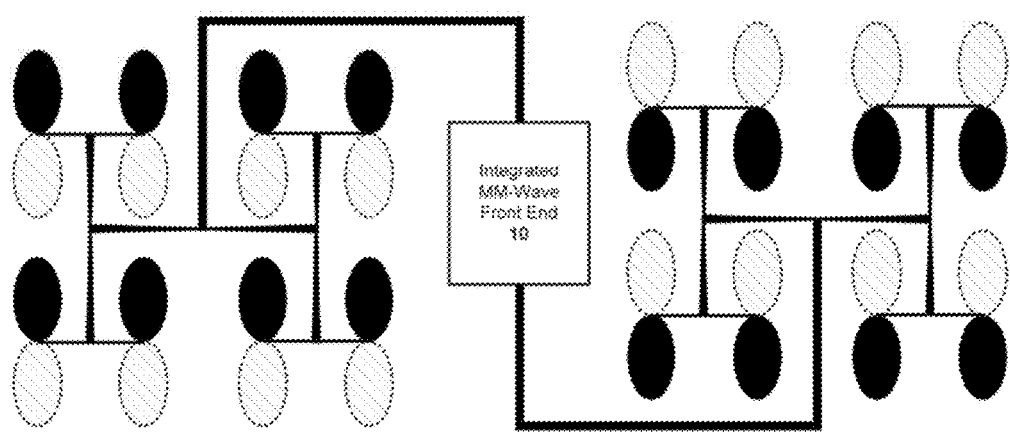
FIG. 6 presents the preferable antenna arrangement for Apparatus 100.

The typical radiation antenna arrangement advantageously proposed for the realization option regarding applications scenarios has 8 dipoles for RX and 8 dipoles for Tx as shown in FIG. 6. This compromise between the directivity, losses in feeding and size, will lead to sensor size of about 4×2×1 cm or less for 60 GHz ISM Band application in Short range device regulation, for worldwide operation. This size and arrangement is particularly interesting for the applications where the distance to the object from antenna is between 50 cm (like transportation vehicle, and integration in portable device) up to 1 to 1.5 m for security applications. For cases where more than 1 m distance to the object is required, more directivity is proposed, which would need larger number of the radiation elements. In that case 32 dipoles for Rx, TX may be used, which would lead to the sensor size of 8×4×1 cm or smaller. Due to the size in that case is more practical to use the sensor as fixed device, or being integrated in larger fixed device like TV sets or displays. More directivity is not primarily important to get enough S/N ration for signal detection, it is rather important to get the reflections from one object and not from more object being close one to another, which would need more complex signal processing and differentiation of the vital signs related to the specific objects.

The proposed antenna system, includes planar high-gain antenna structure, with planar dipols arrangement being fed by planar strip feedings. Behind the plane with dipoles the reflector plane with the distance about one quarter wavelength to the center frequency is present, where the wavelength is related to the propagation properties of the material between the plane of the radiation dipoles and reflector. In case of free space or foam with Er of about 1, the wave length is related to free space propagation. In all of the cases planar dipoles may be realized by the plurality of the technology realization options, and geometrical shapes, or instead of each particular mentioned dipole micro strip like patch antenna is used, by the plurality of the realization options and geometrical shapes. The feeding network connecting dipoles or patches may be realized by the plurality of the realization options and geometrical shapes.

In all of the cases planar dipoles may be realized by the plurality of the technology realization options, and geometrical shapes, or instead of each particular mentioned dipole micro strip like patch antenna is used, by the plurality of the realization options and geometrical shapes. The feeding network connecting dipoles or patches may be realized by the plurality of the realization options and geometrical shapes. Preferably we are proposing using dipoles, being released in the way the one part of the dipoles is on one side of the dielectric support structures and second part of the other dielectric support structure, and where the feeding is performed by symmetrical microstrip line having strips on one and other respective part of the dielectric support structure, and where the matching of the antenna radiation elements (dipoles or patches) impedances is realized by the tapering the symmetrical microstrip lines from thicker lines to thinner lines and vice versa, by the plurality of the tapering approaches.

The Apparatus 100 is inherently low size, low power consumption and low cost operation apparatus is especially proposed for the observation distances from 0.5 m to 3 m distance, typically in 0.5-1 m range.

The digital part includes arbitrary digital wired interface, typically CAN and/or LIN and and/or SPI interface, realized by the plurality of the technologies, allowing easy connection to the world outside the apparatus 100, with cable connection.

The means of short range wireless connection 63 is optional.

The wireless short range communication interface 63 may be realized by two groups of the wireless communication systems:
  a) Short range communication system (typically up to 2 km) having one or more those technologies:
     Short range 433, 866, 915 MHz low data rate commonly worldwide used communication systems
     WIFI, or other 2.4 GHz and 5 GHz Band communication system up to 200 meters.
     Bluetooth
     UWB Systems
     WiMax at 3-4 GHz or in 2-3 GHz range
     Where, typically, pieces of information from more than one Apparatus 100 systems are gathered to the specific concentrator and then further communicated over the long range communication means, by the plurality of their realization.
  b) Long range communication system (typically more than 2 Km) having one or more those technologies:
     Cellular public communication systems with the operation frequencies bellow 3 GHz
     Satellite communication means
     Professional long range communication means with the operation frequencies below 3 GHz
     Radio Link Communication systems with directive antennas with frequencies above 1 GHz Digital and/or wireless interfaces, through of the plurality of their realization, offer:
  a) Remote control of the system, like switching off on, and manual change of the operation modes a) and b).
  b) Information flow toward user about detected event under observation within geographical observation area of the dedicated Apparatus 100, with probability of event detection or values leading for decision of recognizing particular event or more than one event, or with full signal allowing external signal processing outside of the Apparatus 100, but with the same digital processing algorithm.
  c) Identification of the Apparatus 100, giving pre-known information about Apparatus 100 geographical position and its observation area.
  d) Other information about Apparatus 100 status, like: self-function test, operation test, energy management.

The invention claimed is:

1. A mm-Wave Emotion Sensor Apparatus, wherein the mm-wave declares operation between 30 and 300 GHz, the mm-wave emotion sensor apparatus includes:
- a high-gain planar antenna for transmitting mm-wave radio signals, wherein the high-gain planar antenna for transmitting mm-wave radio signals has at least two radiation elements;
- a high-gain planar antenna for receiving mm-wave radio signals, wherein the high-gain planar antenna for receiving mm-wave radio signals has at least two radiation elements;
- a integrated mm-wave radio front end, implemented in a arbitrary semiconductor technology, having on-chip integrated mm-wave voltage control oscillator, mm-wave power amplifier, mm-wave low-noise amplifier, mm-wave IQ demodulator, digital control interface, power supply;
- analog to digital conversion entity;
- digital processing functionality including controlling functionality and calculation and memory capacity for performing digital signal processing by arbitrary type of the realization options;
- interface to entity outside of the apparatus;
- supporting circuitry, including mechanical interface to environment, where the apparatus is working, and supporting electronic circuitry for power supply;
- where apparatus observes area, with direct line-of-sight operation, where the apparatus performs:
  - transmission of mm-wave signals generated in Integrated mm-wave radio front end using the high-gain planar antenna for transmitting mm-wave radio signals;
  - receiving mm-wave signals reflected from observation area using the high-gain planar antenna for receiving mm-wave radio signals;
  - amplification of a reflected signal in the Integrated mm-wave radio front end;
  - down-conversion of signals by mixing with a same signal of the same frequency as a transmitted signal in the Integrated mm-wave radio front end;
  - amplification of a converted signal after mixer in the Integrated mm-wave radio front end;
  - analog filtering of the signals after amplification in the Integrated mm-wave radio front end;
  - signal conditioning in the Integrated mm-wave radio front end for subsequent analog to digital conversion performed by Analog to digital conversion entity;
  - digital processing of the signal in Digital processing functionality, by:
    - extracting a heartbeat rate from a previous processed signal;
    - extracting the rate of a change of the heartbeat rate from a previous arbitrary processed signal;
    - extracting a respiration rate from the previous arbitrary processed signal;
    - extracting the rate of a change of the respiration rate from the previous arbitrary processed signal;
    - digital processing in Emotion calculation functionality, which includes the following steps:
      - evaluation if the heartbeat rate is within a specified range;
      - evaluation if the respiration rate is within the specified range;
      - evaluation if the rate of a change of the heartbeat rate is within the specified range;
      - evaluation if the rate of change of the respiration rate is within the specified range;
      - statistical evaluation of a object heartbeat rate data history;
      - statistical evaluation of a object respiration rate data history;
      - use of Time information entity, which provides information on current time, when the processing is done
      - provision of a current heartbeat rate by a entity, and a current rate of change of the heartbeat rate by the entity, to observation object statistic heartbeat rate model entity;
      - provision of the current respiration rate by a entity for respiratory rate evaluation and the current rate of change of the respiration rate by the entity for respiratory rate change evaluation to observation object statistic respiration rate model entity;
    - digital processing steps in emotion calculation emotion event calculation functionality are performed, which:
      - map rates of heartbeat to a specific object profile range for heartbeats, dedicated to local time, being related to excitement, where this action is named activity 1;
      - map rates of heartbeat to the specific object profile range for heartbeats, dedicated to local time, being related to calmness, where this action is named activity 2;
      - map rates of heartbeat to the specific object profile range for heartbeats, dedicated to local time, being related to linear value, between the ranges dedicated to calmness and excitement, being related to a object mood, where this action is named activity 3;
      - map respiration rates to the specific object profile range for respiration rates, dedicated to local time, being related to excitement, where this action is named activity 4;
      - map respiration rates to the specific object profile range for respiration rates, dedicated to local time, being related to calmness, where this action is named activity 5;
      - map respiration rates to the specific object profile range for respiration rates, dedicated to local time, being related to linear value, between the ranges dedicated to calmness and excitement, being related to the object mood, where this action is named activity 6;
      - map heartbeat rate change to the specific object profile range for heartbeat rate changes, dedicated to local time, being related to excitement, where this action is named activity 7;
      - map heartbeat rate change to the specific object profile range for heartbeat rate changes, dedicated to local time, being related to calmness, where this action is named activity 8;
      - map respiration rate change to the specific object profile range for respiration rate changes, dedicated to local time, being related to excitement, where this action is named activity 9;
      - map respiration rate change to the specific object profile range for respiration rate changes, dedicated to local time, being related to calmness, where this action is named activity 10;

map a specific movement pattern to the specific movement pattern profile, being related to a stress behaviour, where this action is named activity 11;

calculates the findings of activities 1 to 11, by processing the calculated information weighted by a specified importance coefficients, which can take value zero, and providing, calculation information with following outputs:

object is excited;

object is calm;

object has mood factor on the linear scale, describing position between object's full excitements and full calmness object is becoming more excited;

object is becoming less excited;

entity for emotion event calculation sends the calculation information to a entity for initiating apparatus actions upon decided event detection;

the entity for initiating apparatus actions upon decided event detection initiates appropriate specified actions of a entity providing interface to external, remote information evaluation, control and action unit and to supporting circuit entity;

wherein object is a human being.

2. The system as claimed in claim 1, wherein the object is an animal.

3. The system as claimed in claim 1, wherein the apparatus is integrated in a mobile portable device with multimedia functionality, facing the human being, with direct line-of-sight operation.

4. The system as claimed in claim 1, wherein the apparatus is positioned in a living environment of the human being, facing the human being, with direct line-of-sight operation.

5. The system as claimed in claim 1, wherein the apparatus is positioned in a public environment, where emotional status of the human being is evaluated for security reasons, where human being is passing through dedicated corridor, with direct line-of-sight operation.

6. The system as claimed in claim 1, wherein the apparatus is on a fixed position, where the emotional status of the human being is evaluated for security reasons, where human being is simultaneously interviewed, with direct line-of-sight operation.

7. The system as claimed in claim 1, wherein the apparatus is attached to a observing person, where emotional status of the human being under observation is emotionally evaluated, with direct line-of-sight operation.

8. The system as claimed in claim 1, wherein the apparatus initiate actions, which will impose changing of the object's emotional status, by the plurality of actions.

9. The system as claimed in claim 8, wherein the apparatus initiate actions, being multimedia content provision to the object.

* * * * *